United States Patent [19]
Kitto

[11] Patent Number: 5,645,836
[45] Date of Patent: Jul. 8, 1997

[54] ANTI-AIDS IMMUNOTOXINS

[75] Inventor: George Barrie Kitto, Austin, Tex.

[73] Assignee: Research Development Foundation, Carson City, Nev.

[21] Appl. No.: 422,578

[22] Filed: Apr. 14, 1995

[51] Int. Cl.6 .................... A61K 39/42; C07K 16/10
[52] U.S. Cl. .................... 424/181.1; 424/183.1; 530/391.7
[58] Field of Search ................... 424/159.1, 160.1, 424/183.1, 188.1, 181.1; 435/70.21, 172.1, 240.37; 530/388.3, 388.35, 389.4, 391.7

[56] References Cited

PUBLICATIONS

Ervice et al. (1993) Antimicrobial Agents and Chemotherapy. vol. 37 No. 4 835–838.
Laurence et al (1987) Science vol. 235 1501–1504.
Zarling et al (1990) Nature vol. 347 92–95.
Fahey et al (1992) Clin Exp. Immunol. vol. 88 1–5.
Fox, JL. (1994) Bio/Technology vol. 12 p. 128.
Waldmann, TA. (1991) Science vol. 252 pp. 1657–1662.
Harris et al. (1993) TibTech vol. 11 pp. 42–44.
Ferns et al. (1991) AIDS Research and Human Retroviruses. vol. 7 No. 3 pp. 307–313.
Blakey, DC et al. (1988) Waldman H (ed.): Monoclonal Antibody Therapy: Prog. Allergy. Basel Karger vol. 45 pp. 50–90.
Restle et al. (1992) J. Biol. Chem. vol. 267 No. 21 14654–16661.
Olson et al. (1991) AIDS Research and Human Retroviruses. vol. 7 No. 12 1025–1030.

Primary Examiner—Lila Feisee
Assistant Examiner—Julie E. Reeves
Attorney, Agent, or Firm—Benjamin Aaron Adler

[57] ABSTRACT

The present invention provides a novel anti-AIDS immunotoxin. The immunotoxin comprises a toxin chemically conjugated to a monoclonal antibody directed against vital reverse transcriptase. Also provided are various methods of using this novel including methods of treating various diseases.

3 Claims, 8 Drawing Sheets

ANTI-AIDS IMMUNOTOXINS

BACKGROUND OF THE INVENTION

1. Field of the Invention

The present invention relates generally to the fields of molecular immunology and therapies for the Acquired Immune Deficiency Syndrome (AIDS). More specifically, the present invention relates to novel immunotoxins for the treatment of AIDS.

2. Description of the Related Art

With more than six million people worldwide infected with the HIV virus, effective therapies for this disease are desperately needed. While research on developing vaccines is being actively pursued, the nature of the virus makes this an exceptionally difficult, long term task. Moreover, treatment of current AIDS cases is severely limited. Only one drug, azidothymidine (AZT) is currently registered for the full use in the U.S. There are however problems with strains of HIV resistant to AZT developing. As mutant forms of the virus appear, the degree of resistance increases. The prevailing theory on virus resistance was that the virus mutated at such rapid rates that more resistant forms appeared rather quickly. Recent studies, however, suggest that this resistance is not a result of hypermutability, but possibly a consequence of the high level of replication of the virus.

Regardless of the mechanisms of resistance, AZT is not effective for a long period of time. This treatment is also extremely expensive and has several accompanying side effects such as nausea, seizures, liver function abnormalities, and bone marrow suppression. Other chemical variants of AZT, such as DDC and DDI, show promise in clinical trials but are, however, of limited effectiveness. Although a number of other drugs and treatment regimes are being investigated, there is clearly a pressing need for additional drugs and new approaches to treating this disease.

Experimental immunotherapy approaches to AIDS have shown some promise, but most exhibit very wide variability of effectiveness, primarily because of the highly variable nature of the target molecules. These target molecules, such as the HIV envelope proteins, vary from strain to strain and from patient to patient.

Immunotoxin therapy has, however, proven very effective against several other diseases when there is an absolutely specific target for the antibody portion of the antibody-toxin conjugates. For example, the Pseudomonas exotoxin was coupled to a monoclonal antibody targeted against ovarian cancer tumors. It effectively inhibited the growth of human ovarian cancer cells in a mouse model (Willingham, M. C., et al., 1987). What is needed for AIDS immunotherapy is a highly specific and unvarying target.

The HIV enzyme reverse transcriptase (RT) is of absolutely critical importance for viral replication. The enzyme plays an essential role in catalyzing the formation of a DNA copy of the viral genetic material (RNA). The DNA is then used either for generating more copies of the virus immediately or for integration into the patient's genome, for later expression of the disease. This critical role of reverse transcriptase is likely the reason for its highly conserved structure. Moreover, it was recently shown that, when cells are infected with HIV, copies of the reverse transcriptase (or portions thereof) are attached to the exterior cell surface. The cell surface expression of the reverse transcriptase is markedly greater than that for even the viral envelope proteins.

The prior art is deficient in the lack of effective means of therapeutically treating the acquired immune deficiency syndrome. The present invention fulfills this longstanding need and desire in the art.

SUMMARY OF THE INVENTION

In one embodiment of the present invention, there is provided a composition of matter, comprising an immunotoxin, said immunotoxin comprising a toxin chemically conjugated to a monoclonal antibody directed against viral reverse transcriptase.

In another embodiment of the present invention, there is provided a pharmaceutical composition, comprising an immunotoxin, said immunotoxin comprising a toxin chemically conjugated to a monoclonal antibody directed against viral reverse transcriptase and a pharmaceutically acceptable carrier.

In still yet another embodiment of the present invention, there is provided a method of treating the Acquired Immune Deficiency Syndrome comprising the step of administering to a human having said syndrome a pharmacologically effective dose of the novel composition of the present invention.

In another embodiment of the present invention, there is provided a method of treating an individual infected with the Human Immunodeficiency Virus comprising the step of administering to said individual a pharmacologically effective dose of the novel composition of the present invention.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the general immunotoxin synthetic scheme (FIGS. 1A, 1B, 1C, 1D)

FIG. 2 shows the transcriptase monoclonal antibody-Pokeweed antiviral protein immunotoxin directed against an HIV strain (HIV-AC-1) infecting H9 cells with exposure of the cells to the immunotoxin for either 24 or 48 hours.

FIG. 3 shows the effects of the anti-reverse transcriptase monoclonal antibody-Pokeweed antiviral protein immunotoxin on the HIV cell line H-9 and HIV strain, PM-213 after exposure of the cells to the immunotoxin for either 24, 48 or 72 hours.

FIG. 4 shows a dose response relationship for cytotoxicity for the anti-reverse transcriptase monoclonal antibody-Pokeweed antiviral protein immunotoxin construct of the present invention after 1 day of incubation.

FIG. 5 illustrates a dose response relationship for cytotoxicity for the anti-reverse transcriptase monoclonal antibody-gelonin immunotoxin of the present invention.

FIG. 6 shows the effect of the anti-reverse transcriptase monoclonal antibody-Pokeweed antiviral protein immunotoxin on H9 cells +HIV-IIIB.

FIG. 7 shows the effect of treating H9+MN cells for 3 days with the anti-reverse transcriptase monoclonal antibody-pokeweed antiviral protein immunotoxin of the present invention.

DETAILED DESCRIPTION OF THE INVENTION

Figure 1:
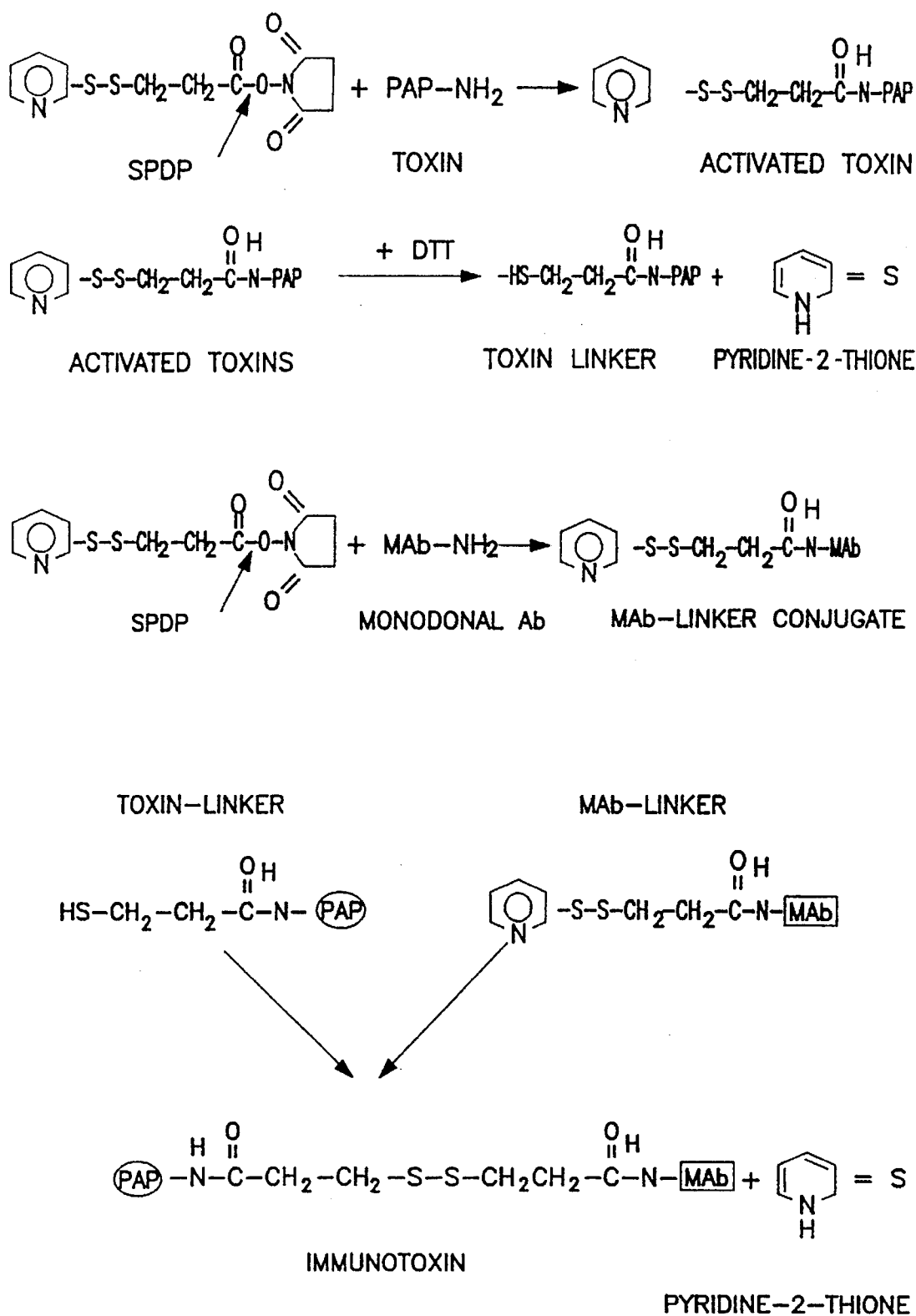

This present invention discloses the development of a new approach to immunotoxin therapy of the Acquired Immune Deficiency Syndrome (AIDS). The design of the therapeutic pathway is based on delivery of extremely potent toxins specifically to cells infected with the AIDS virus, by targeting the infected cells using monoclonal antibodies directed against the viral reverse transcriptase.

A very high percentage of HIV infected cells express the viral reverse transcriptase on the cell surface. Also, the HIV reverse transcriptase varies in structure very little from strain to strain and from isolate to isolate. This is unlike most of the HIV viral proteins, which are exceptionally variable. The present invention discloses immunotoxins prepared using different monoclonal antibodies against the HIV-1 reverse transcriptase and a variety of both single and double chain, catalytic ribosome inactivating toxins, including poke-weed antiviral protein, gelonin ricin A chain, modeccin and dodecandrin.

The efficacy of an immunotoxin is a function of both antibody and toxin. Factors governing cell binding, internalization, translocation from surface to interior and overall cytotoxicity are complicated and often unpredictable. It is very difficult, therefore, to determine which monoclonal antibody should be conjugated to a specific toxin.

The present invention establishes optimal dose response curves for the MAb-PAP (Pokeweed antiviral protein) and MAb-Gelonin immunoconjugates. These dose response curves facilitate comparison with other types of immunoconjugate preparations. The present invention also discloses preparation of immunoconjugates, prepared with the same monoclonal antibody, but containing the toxins ricin, ricin A chain, and dodecandrin, for their cytotoxic potential against HIV-infected cells.

The present invention discloses additional monoclonal antibodies against HIV-1-reverse transcriptase. These monoclonals are then each coupled to PAP (Pokeweed antiviral protein), gelonin, ricin, ricin-A chain or dodecandrin and subjected to cytotoxicity testing.

The present invention describes a composition of matter, comprising an immunotoxin, said immunotoxin comprising a toxin chemically conjugated to a monoclonal antibody directed against viral reverse transcriptase. A panel of more than 70 mouse monoclonal antibodies have been prepared against HIV-1 reverse transcriptase. These differ in IgG and IgM classes and subtype. Representative examples of monoclonal antibodies specific for HIV reverse transcriptase include: HIVRT 10-1-a, HIVRT 2-2-F8, HIVRT 11-1-b, HIVRT 6-1-a, HIVRT 12-1-c, HIVRT 6-9, HIVRT 15-3, HIVRT 16-4, HIVRT 14-1-d, HIVRT 18-1, HIVRT 2-3-b, HIVRT 10-1-b and HIVRT 10-4.

The present invention also provides a method of treating the Acquired Immune Deficiency Syndrome comprising the step of administering to a human having said syndrome a pharmacologically effective dose of the composition of claim 4.

Also, the present invention provides a method of treating an individual infected with the Human Immunodeficiency Virus comprising the step of administering to said individual a pharmacologically effective dose of the composition of the present invention.

It is specifically contemplated that pharmaceutical compositions may be prepared using the novel immunotoxins of the present invention. In such a case, the pharmaceutical composition comprises the novel immunotoxins of the present invention and a pharmaceutically acceptable carrier. A person having ordinary skill in this art would readily be able to determine, without undue experimentation, the appropriate dosages and routes of administration of the different immunotoxins disclosed by the present invention.

A pharmaceutical composition, comprising the novel immunotoxins of the present invention and a pharmaceutically acceptable carrier is also provided. The pharmaceutical compositions of the present invention are suitable for use in a variety of drug delivery systems. For a brief review of present methods for drug delivery, see Langer, *Science*, 249:1527–1533 (1990). Methods for preparing administrable compounds will be known or apparent to those skilled in the art and are described in more detail, for example, in Remington's *Pharmaceutical Science*, 17th ed., Mack Publishing Company, Easton, Pa. (1988).

In any treatment regimen, the immunotoxins of the present invention may be administered to a patient either singly or in a cocktail containing two or more immunotoxins, other therapeutic agents, compositions, or the like, including, but not limited to, immunosuppresive agents, tolerance-inducing agents, potentiators and side-effect relieving agents. Particularly preferred are immunosuppressive agents useful in suppressing allergic reactions in a host. Preferred immunosuppressive agents include prednisone, prednisolone, DECADRON, cyclophosphamide, cyclosporine, methotrexate and azathiprine. Preferred potentiators include monensin, ammonium chloride, perhexiline, verapamil and amantadine. All of these agents are administered in generally accepted efficacious dose ranges as is well known in the art. Additionally, if patients did express an immune response to a specific immunoconjugate then alternate immunoconjugates, differing in either or both the monoclonal antibody or toxin component could be employed sequentially.

The immunotoxins of the present invention may be administered after formulation into an injectable preparation. Parenteral formulations are known and are suitable for use in the invention, e.g., intramuscular or intravenous administration. The formulations containing therapeutically effective amounts of immunotoxins are either sterile liquid solutions, liquid suspensions or lyophilized versions, and optimally contain stabilizers and excipients. Lyophilized compositions are reconstituted with suitable diluents, e.g., water for injection, saline, 0.3% glycine and the like, at a level of about from 0.01 mg/kg of host body weight to 10 mg/kg where the biological activity is less than or equal to 20 ng/ml when measured in a reticulocyte lysate assay. Typically, the pharmaceutical compositions containing immunotoxins of the present invention is in a range of from about 0.01 mg/kg to about 5 mg/kg body weight of the patient administered over several days to about two weeks by daily intravenous infusion. The precise concentration to be used in the vehicle is subject to modest experimental manipulation in order to optimize the therapeutic response.

The immunotoxins of the present invention may be administered by aerosol to achieve localized delivery to the lungs. This is accomplished by preparing an aqueous aerosol, liposomal preparation or solid particles containing immunotoxin. Ordinarily, an aqueous aerosol is made by formulating an aqueous solution or suspension of immunotoxin together with conventional carriers and stabilizers. The carriers and stabilizers vary depending upon the requirements for the particular immunotoxin, but typically include: nonionic surfactants, innocuous proteins, e.g., albumin, sorbitan esters, lecithin, amino acids, e.g., glycine, and buffers, salts, sugars or sugar alcohols.

Alternatively, immunotoxins of the present invention may be administered orally by delivery systems such as proteinoid encapulation as described by Steiner, et al., U.S. Pat. No. 4,925,673. Typically, a therapeutically effective oral dose of an immunotoxin of the present invention is in the range of about 0.01 mg/kg body weight to about 50 mg/kg body weight per day. A preferred effective dose is in the range from about 0.05 mg/kg body weight to about 5 mg/kg body weight per day.

Th imunnotoxins of the present invention may be administered in solution. The pH of the solution should be in the range of pH 5 to 9.5, preferably pH 6.5 to 7.5. The immunotoxin or derivatives thereof should be in a solution having a suitable pharmaceutically-acceptable buffer such as phosphate, Tris(hydroxymethyl)aminomethane HCl or citrate or the like. Buffer concentrations should be in the range of 1 to 100 mM. The immunotoxin solution may also contain a salt, such as sodium chloride in a concentration of 50–150 mM. An effective amount of a stabilizing agent such as albumin, a globulin, a gelatin, a protamine or a salt of protamine may also be included.

The present invention also provides a method of treating the Acquired Immune Deficiency Syndrome (AIDS) disease in a human comprising the step of administering to a human a pharmacologically effective dose of an immunotoxin of the present invention designed to inhibit the replication of the HIV virus.

The following examples are given for the purpose of illustrating various embodiments of the present invention and are not meant to limit the present invention in any fashion.

EXAMPLE 1

Preparation of Toxins

Each of the toxins envisioned for use as part of the immunotoxins can be purified by standard published procedures. The procedures used to purify the ribosome inactivating proteins from extracts are similar for all these proteins. The proteins are predominantly basic in charge and do not bind to anion exchange resins such as DEAE- cellulose. Typical methodologies for poke-weed antiviral protein are given in: Irvin, J. D., *Arch. Biochem. Biophys.* 169, 522–528 (1975); Irvin, et al., *Arch. Biochem. Biophys.*, 200, 418–425 (1980); Barbieri, et al., *Biochem. J.*, 203, 55–59 (1982); For gelonin, methods are given in : Lambert, J. et al in "Immunotoxins" pg 177 (1988) Stirpe, et al., *J. Biol. Chem.* 255, 6947–6953 (1980) and for dodecandrin in Ready, et al., J. D. Biochim. Biophys. Acta 791, 314–319 (1984). For ultra high purity, as will be required for possible clinical trials, an antibody affinity column has been devised for PAP. This technology can readily be adapted for the other toxins.

EXAMPLE 2

Preparation of HIV-reverse transcriptase

HIV-reverse transcriptase can be prepared according to the method of Kohlstaedt and Steitz, *Proc. Natl. Acad. Sci.*, 89:1259 (1989). The purification scheme used to prepare HIV-reverse transcriptase utilizes an reverse transcriptase expression clone described by Summers and D'Aquila (1989) and was obtained through the AIDS Research and Reference Reagent Program, Division of AIDS, NIAID, NIH: Reagent Number pKRT2, Catalog Number 393, contributed by Dr. Richard D'Aquila and Dr. William C. Summers.

EXAMPLE 3

Preparation of Monoclonal Antibodies

A typical protocol for the production of hybridoma cell lines was as follows. Two male (RTI and RTII) and two female (RTIII and RTIV) six week old balb/c mice were pre-bled for a negative control, and then each was injected with 10 micrograms of recombinant HIV-1 reverse transcriptase. The purity of this protein was checked on an SDS gel. Each mouse was boosted with reverse transcriptase 3 times at 2 micrograms/boost. A sample bleed from each mouse was then extracted and found to have titers ranging from 60,000 to 80,000 (see below for methodology). The two female mice were sacrificed and their spleens were removed. The cells extracted from the immunized spleens were fused with mouse myeloma cells. These fused cells were grown on selective media (1×HAT) which does not allow the growth of myeloma fused myeloma cells. This media contains hypoxanthine, aminopterin, and thymidine. The myeloma fused spleen cells are referred to as hybridomas. Each parent hybridoma was tested using the ELISA method (see below for Indirect ELISA). The hybridomas that tested positive were assayed a second time. Once the hybridoma tested positive a second time, a portion of this parent clone was grown up (expanded) and then frozen; a second portion was subcloned. These first subclones were also tested using the ELISA method. The first subclones that tested positive were expanded and frozen and a fraction was subcloned again. The second subclones that tested positive were also expanded and frozen. The supernatant from these positive testing second subclones contained monoclonal antibodies that could be extracted and purified.

EXAMPLE 4

Testing for Mouse Serum Antibody Titer Using Indirect ELISA

The reverse transcriptase antigen was diluted so that each well on a flat-bottomed 96-well microtiter plate (NUNC-Immunoplate, Thomas Scientific) contained 50 nanograms of antigen. The antigen was incubated for 1 hr at room temperature. After incubation, the antigen was shaken out, and the wells were blocked with 100 μl blocking buffer/well (0.1M potassium phosphate 0.5% Tween 20, 1% bovine serum albumin, pH 7.0) at room temperature for 30 minutes. The plate was washed three times (washing buffer—0.1M potassium phosphate, 0.5% Tween, pH 7.0), and the diluted serum samples were added and incubated overnight at 4° C. The range of dilution was 1:250 to 1:80,000. The following day everything was brought to room temperature, the plate was washed and a 1:1000 dilution of Peroxidase-conjugated AffiniPure Donkey Anti-mouse IgG (Jackson ImmunoResearch Laboratory, Inc.) was prepared. This was added to each well, and the plate was incubated for thirty minutes at room temperature. Again the plate was washed, and 100 microliters of substrate solution (0.7 mg/ml of 2,2'-aminobis [3-ethylbenz-thiazoline-6-sulfonic- acid] diammonium salt [ABTS]) (Moss, Inc.) was added per well for 20 minutes. The reactions were then stopped by the addition of 100 microliters of oxalic acid/well. Absorbances were read at 414 nm using an ELISA reader (BioRad, model 2550). The optical density (OD) reading to correspond with a positive result was taken to be greater than 0.500, and all four mice had titers of 1:80,000 on this scale.

EXAMPLE 5

Screening for Positive Hybridomas

The screening procedure for detecting positive hybridomas by assay of cell supernatants followed the same protocol as that of the indirect ELISA. Cell supernatant samples were diluted 1:1 with 100 microliters of washing buffer (0.1M potassium phosphate, 0.05% Tween-20, 1 mg/ml bovine serum albumin, pH 7). The antigen used was purified reverse transcriptase and 50 nanograms were dispensed per well. All positives from the first subclone were re-tested, and if they gave positive results again, they were subcloned a second time. The second subclones were also tested using the ELISA method. Once a second subclone tested positive twice, it was expanded and frozen for later use in the production of the monoclonal antibodies.

EXAMPLE 6

Monoclonal Antibody Ascites Fluid Production

Six week old female balb/c mice were used for the production of ascites fluid. They were primed for production by first injecting with pristane. Twelve mice were injected with the hybridoma HIVRT-10-1-a. After 10 days, a noticeable swelling occurred in the peritoneal cavity of the mice. This indicated the presence of a soft, fluid-filled tumor which could be drained using a 20½ gauge Precision Glide needle to remove the ascites fluid. The needle was inserted into the peritoneal cavity near the upper part of the leg. Each day the puncture point was altered to alleviate as much discomfort as possible. The amount of ascites collected per mouse ranged from ~0.2 ml to 3.0 ml. The ascites fluid collected on the same day from the same group of mice was combined. The ascites fluid was then centrifuged in a Sorvall Superspeed RC2-B Centrifuge in a Sorvall GSA rotor at 3000 g in sterilized, prebalanced 15 ml tubes for 15 minutes. The fat layer was removed from the top, and the ascites fluid was separated from the cellular debris pellet at the bottom. The collection was terminated when the soft, fluid-filled tumor became hard, and ascitic fluid was no longer draining from the cavity. At this point the mice were killed. The ascites fluid from the each hybridoma line was then combined. The ascites fluid was stored at 4° C. in a sterilized tube.

EXAMPLE 7

Purification of Monoclonal Antibody Using Protein G

Mouse ascites fluid from the HIVRT-10-1-a hybridoma line was run on a Protein G column. The Protein G—Sepharose 4B was purchased from Sigma, product number 54HO145. All Protein G procedures were carried out at 4° C. according to the manufacturers' protocols. In order to estimate the concentration of protein in the monoclonal antibody fractions, the Bradford assay (Bradford, M., 1976) was employed. A micro version of this assay was used, which was obtained commercially through Bio-Rad (no. 500-0006) (BioRad, 1984). The purity of the final antibody was checked using SDS polyacrylamide electrophoresis and found to be greater than 95%.

EXAMPLE 8

Immunotoxin Synthetic Scheme

Synthesis of the immunotoxins is carried out by the general procedural steps of: (1) Coupling of Toxin to Linker (FIG. 1A); (2) Coupling of Monoclonal Antibody to Linker (FIG. 1B); (3) Reduction of Toxin+Linker (FIG. 1C); and (4) Linkage of Toxin and Monoclonal Antibody (FIG. 1D). The typical chemistry employed is illustrated in FIG. 1. Each of the above-described steps must be carried out with high yield and with purification of the products if the overall synthesis is to be satisfactorily achieved. In the present instance, the plant toxins were linked to monoclonal antibodies by a disulfide bond with N-succinimidyl 3-(2-pyridyldithio)-propionate (SPDP), to give an average ratio of toxin to antibody within the range 1–2:1. This technology has proven both reproducible and effective in providing immunotoxins which are uniformly conjugated. A detailed methodology for the preparation of a monoclonal antibody-pokeweed antiviral protein conjugate is described below.

EXAMPLE 9

Preparation of 2-Pyridylthiopropionyl-PAP (PDP-PAP)

PDP-PAP was prepared by reacting 0.16 mM PAP with 0.48 mM SPDP in a final volume of 0.200 ml buffered with 40 mM sodium phosphate, pH 7.0. After incubation for one hour at 37° C., the mixture was separated on a HPLC Protein Pak 300SW equilibrated with 50 mM potassium phosphate, pH 6.0. Fraction volumes of 1 ml were collected for 25 minutes. Peak fractions were concentrated with the Speedvac. A portion of this PDP-PAP concentrated fraction was run on gel electrophoresis to test for purity.

EXAMPLE 10

Preparation of PDP-antibodies

Monoclonal antibodies were incubated with a three fold molar excess of SPDP for 1 hour at 37° C. in 40 mM sodium phosphate, pH 7.0. The sample was then fractionated through a size exclusion HPLC column equilibrated with 50 mM potassium phosphate, pH 6.0. Twenty-five 1 ml fractions were collected for a time of 25 minutes. The peak fractions were concentrated using the Speedvac. A small sample of PDP-MAb was run on SDS gel electrophoresis to check for purity.

EXAMPLE 11

Preparation of PDP-antibodies

Monoclonal antibodies were incubated with a three fold molar excess of SPDP for 1 hour at 37° C. in 40 mM sodium phosphate, pH 7.0. The sample was then fractionated through a size exclusion HPLC column equilibrated with 50 mM potassium phosphate, pH 6.0. Twenty-five 1 ml fractions were collected for a time of 25 minutes. The peak fractions were concentrated using the Speedvac. A small sample of PDP-MAb was run on SDS gel electrophoresis.

A wide variety of cross-linking substances may be used to chemically link the monoclonal antibody to the toxin in the methods described in the present invention. Representative examples of suitable cross-linking agents include m-maleimidobenzoyl-N-hydroxysuccinimide ester (MBS), N-succinimidyl-3-(2-pyridyldithio-)-propionate (SPDP), alpha-iminothiolane hydrochloride, methyl 3-mercaptopropionimidate, Succinimidyl 4-(N maleimidomethyl)cyclohexame-1-carboxylate (SMCC), 4-succinimidyloxycarbonyl-alpha-methyl-alpha-(2- pyridydithio)-toluene (SMPT), N-succinimidyl(4-iodoacetyl)aminobenzoate (SIAB) and sulfosuccinimidyl 4-(p-maleimidophenyl)butyrate (SMPB).

A wide variety of toxins may be chemically linked to the monoclonal antibodies described herein. Representative examples of suitable toxins include Pokeweed antiviral protein, gelonin, ricin, abrin, modeccin, dodecandrin, saporin, volkensin and vicumin.

Alternatively, an immunoconjugate of the present invention may be a fusion protein prepared by genetic engineering methods known to those in the art. Such a fusion protein would contain the antigen recognition site of an antibody molecule and the cytotoxic moiety of a toxin.

EXAMPLE 12

Cytotoxicity of the Immunoconjugates

The efficacy of the conjugates to specifically kill infected cells versus non-infected cells was demonstrated against a variety of cell lines in vitro. Various concentrations of the immunotoxins were added to one or more cultures of the uninfected and correspondingly chronically-infected cells, the latter of which have recovered from any cytopathic effects of virus infection. Cell viability and cell growth were monitored daily by propidium iodide exclusion and light scattering on an EPICS Profile flow cytometer.

Three separate series of cytotoxicity trials were carried out using disulfide linked immunoconjugates of pokeweed antiviral protein and gelonin, prepared as described above and tested against different cell lines and/or different HIV strains. Representative examples of these cytotoxicity tests are shown below.

FIG. 2 and TABLE I show the results of testing varying amounts of an anti-reverse transcriptase monoclonal antibody-Pokeweed antiviral protein immunotoxin directed against an HIV strain (HIV-AC-1) infecting H9 cells with exposure of the cells to the immunotoxin for either 24 or 48 hours. After 24 hours of incubation, the anti-reverse transcriptase monoclonal antibody-Pokeweed antiviral protein immunotoxin killed about 65% of HIV-infected cells but only about 15% of uninfected (control) cells. Furthermore, after hours incubation, the anti-reverse transcriptase monoclonal antibody-Pokeweed antiviral protein immunotoxin killed about 95% of HIV-infected cells but only about 20% of uninfected (control) cells. Of note is the high specificity of the immunotoxin for HIV infected cells.

TABLE I

Immunotoxin directed against the AC-1 Strain

| Days Post- | | | % Dead Cells | | |
|---|---|---|---|---|---|
| Treatment | Target Cell | Media | 1 μl | 10 μl | 100 μl |
| 1 | H9 | 4% | 3% | 5% | 17% |
| | H9+AC1 | 4% | 19% | 32% | 68% |
| 2 | H9 | 6% | 4% | 6% | 23% |
| | H9+AC1 | 6% | 15% | 48% | 96% |

FIG. 3 and TABLE II shows the effects of the anti-reverse transcriptase monoclonal antibody-Pokeweed antiviral protein immunotoxin on the HIV cell line H-9 and HIV strain, PM-213 after exposure of the cells to the immunotoxin for either 24, 48 or 72 hours. After 72 hour incubation, the anti-reverse transcriptase monoclonal antibody-Pokeweed antiviral protein immunotoxin killed virtually 100% of HIV-infected cells but only about 20% of uninfected (control) cells.

TABLE II

Immunotoxin directed against the PM213 Strain

| Days Post- | | | % Dead Cells | | |
|---|---|---|---|---|---|
| Treatment | Target Cell | Media | 1 μl | 10 μl | 100 μl |
| 1 | H9 | 3% | 2% | 5% | 2% |
| | H9+213 | 6% | 4% | 8% | 21%· |
| 2 | H9 | 2% | 1% | 4% | 8% |
| | H9+213 | 5% | 8% | 24% | 46% |
| 3 | H9 | 4% | 1% | 3% | 19% |
| | H9+213 | 7% | 12% | 30% | 100% |

The H-9 cell line used for these studies was derived from a single T- cell clone obtained from a specific HUT 78 cell line and selected for its high permissive growth with HIV-1. Further information about this cell line can be found in the National Institutes of Health AIDS Reference Research Reagent Catalog (January 1995). The monoclonal antibody used in the preparation of the immunotoxin employed for the trials shown in FIGS. 2 and 3 was from Dr. M. G. Sarngadharan. Cells were grown and maintained in a carbon dioxide incubator at 37° C.

A second series of trials was carried out using pokeweed antiviral protein (PAP) and gelonin containing immunoconjugates. In this case the monoclonal antibody employed (HIVRT 10-1-a) was prepared at the University of Texas as Austin as described above. Again, the cell line used was H-9 and the HIV strain was PM213 and cytotoxicity testing was carried out in the same fashion. FIG. 4 shows a dose response relationship for cytotoxicity for the anti-reverse transcriptase monoclonal antibody-Pokeweed antiviral protein immunotoxin construct of the present invention after 1 day of incubation. Increasing cytotoxicity toward HIV infected cells was seen as the concentration of immunotoxin was increased. Similarly, FIG. 5 illustrates a dose response relationship for cytotoxicity for the anti-reverse transcriptase monoclonal antibody-gelonin immunotoxin of the present invention. With both the PAP and gelonin containing immunotoxins selective killing of HIV infected cells was observed.

A third and more extensive series of trials was carried out using the same PAP and gelonin containing constructs and the same cytoxicity testing methods as used for the second set of trials. In this set of experiments, the HIV strains HIV-IIIB and HIV-MN were employed in the H-9 cell line and incubations were carried out for 3 days. The HIV-IIIB and MN virus lines are described in the National Institutes of Health AIDS Reference Research Reagent Catalog (January 1995).

FIG. 6 and TABLE III show the effect of the anti-reverse transcriptase monoclonal antibody-Pokeweed antiviral protein immunotoxin on H9 cells +HIV-IIIB. At a dose of 1 nanogram/ml, the pokeweed antiviral protein immunotoxin produced about 77% cell death after 3 days. Approximately 90% of the cells were killed by the 10 nanogram/ml dose. Little toxicity was seen against uninfected cells.

TABLE III

| | PAP IMMUNOTOXIN | | | | |
|---|---|---|---|---|---|
| Days Post-Treatment | Target Cell | Media | % Dead Cells | | |
| | | | 1 | 3.4 | 10 |
| 1 | H9 | 7 | 8 | 11 | 19 |
| | H9+HIVIIIB | 9 | 26 | 30 | 34 |
| | H9+HIV MN | 9 | 12 | 11 | 17 |
| 2 | H9 | 4 | 5 | 9 | 7 |
| | H9+HIVIIIB | 5 | 59 | 65 | 70 |
| | H9+HIV MN | 7 | 25 | 24 | 39 |
| 3 | H9 | 6 | 9 | 12 | 9 |
| | H9+HIVIIIB | 7 | 77 | 89 | 92 |
| | H9+HIV MN | 7 | 51 | 54 | 68 |

H9 is the uninfected cell line. The doses of the immunotoxin are given in μg/ml.

Figure 7:
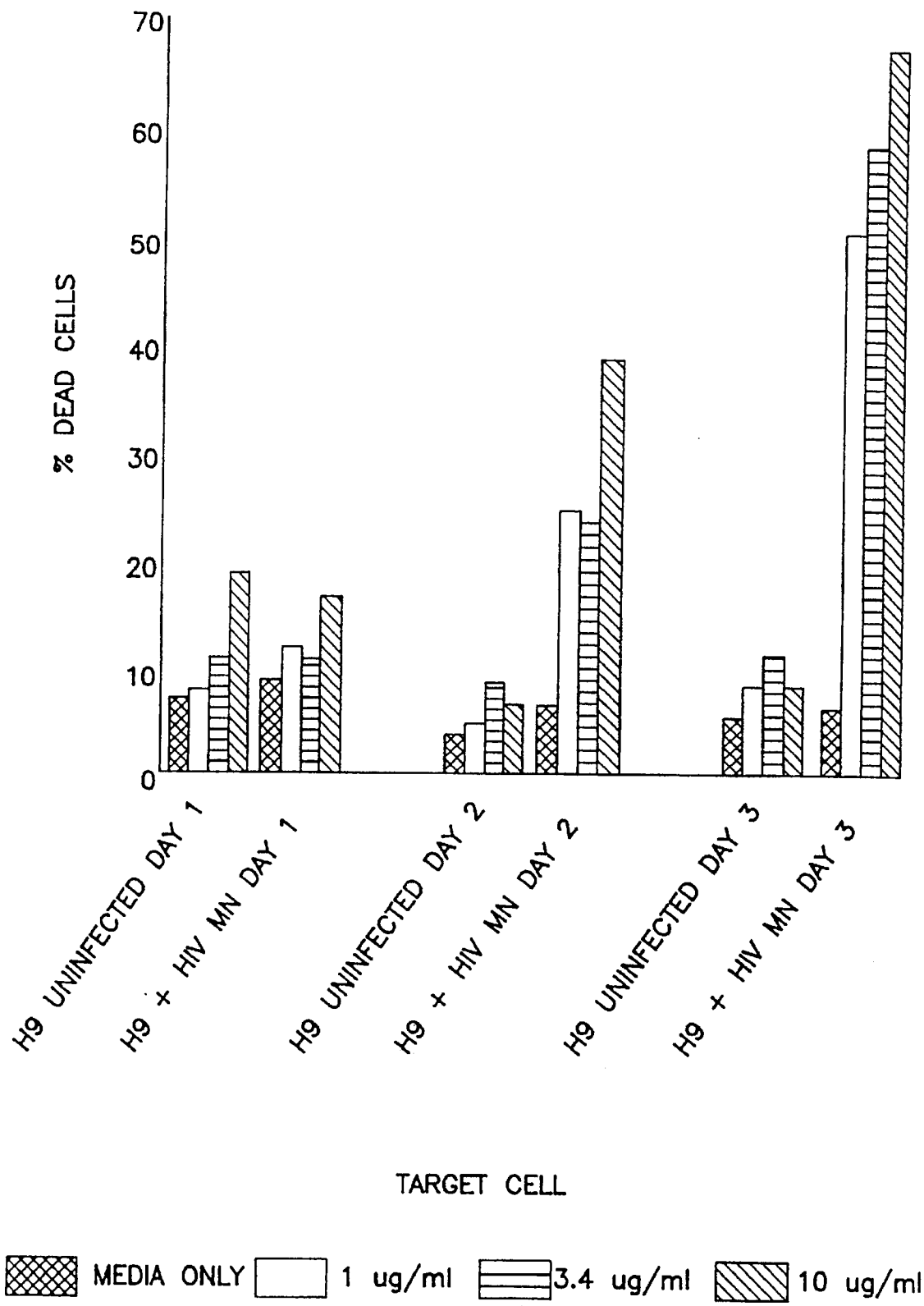

FIG. 7 and TABLE III show the effect of treating H9+MN cells for 3 days with the anti-reverse transcriptase monoclonal antibody-pokeweed antiviral protein immunotoxin of the present invention. At a dose of 1 nanogram/ml, the PAP immunotoxin produced about 50% cell death after 3 days. Approximately 68% of the cells were killed by the 10 nanogram/ml dose at this time period. Again low toxicity against uninfected cells was seen.

Figure 8:
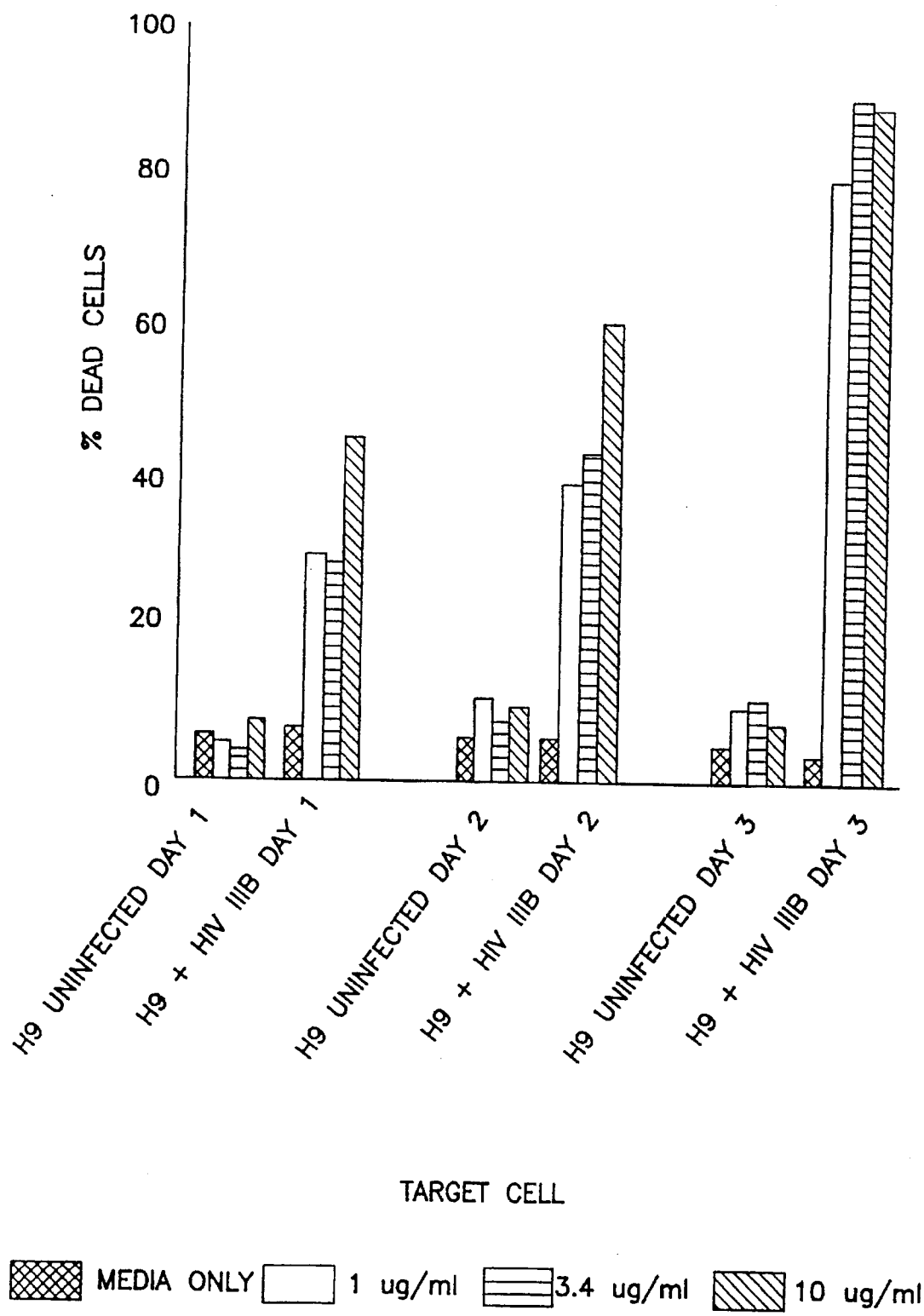
FIG. 8 illustrates the effect of the gelonin immunotoxin of the present invention on H9 cells plus HIV-IIIB over 3 days of incubation.

FIG. 8 and TABLE IV illustrate the effect of the gelonin immunotoxin of the present invention on H9 cells plus HIV-IIIB over 3 days of incubation. By day 3, a dose of 1 nanogram/ml of the gelonin immunotoxin produced approximately 80% cell kill. A 3.4 nanogram/ml dose of this immunotoxin resulted in approximately 90% cell death.

Figure 9:
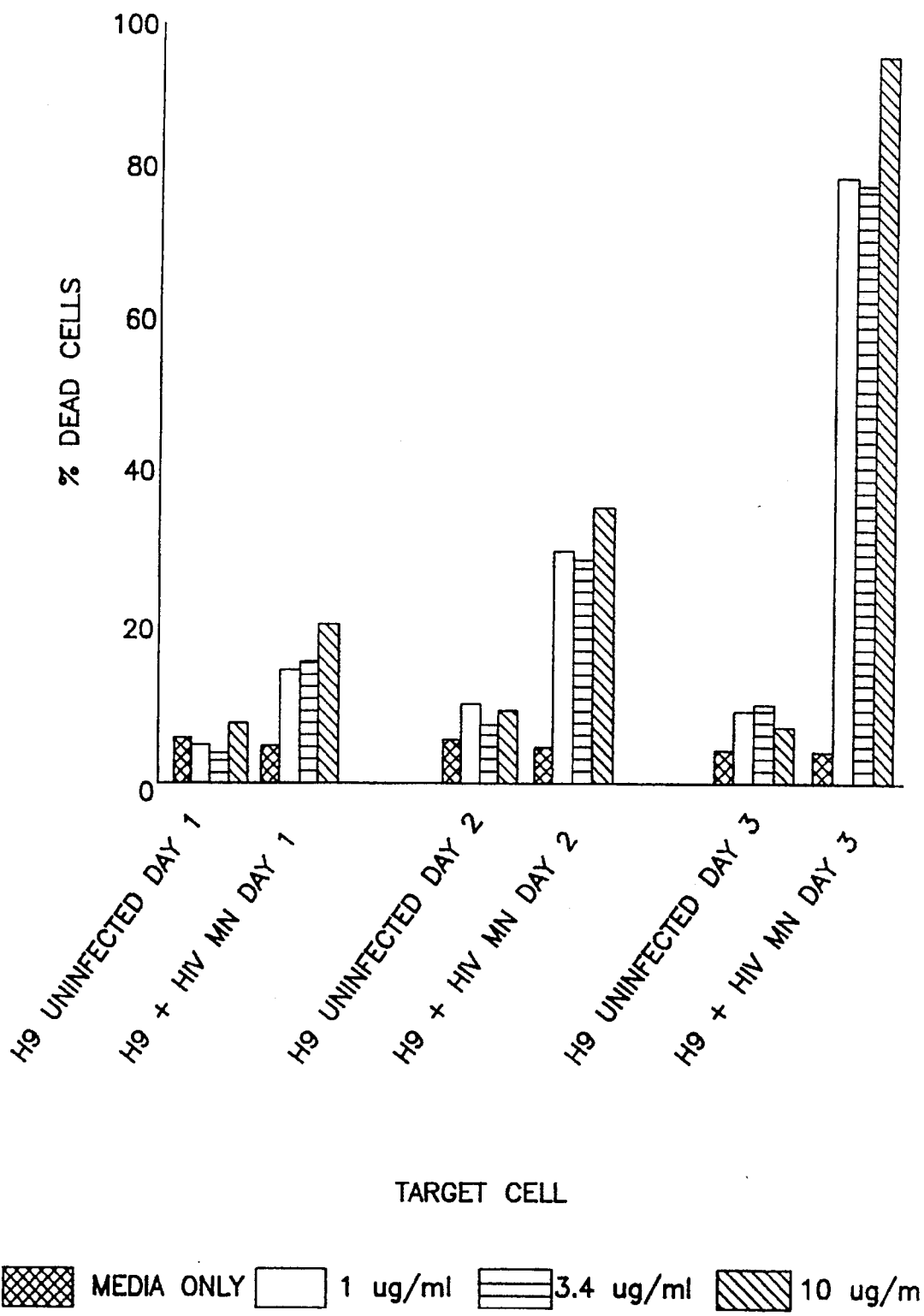
FIG. 9 illustrates the effect of the gelonin immunotoxin of the present invention on H9 cells plus HIV-MN.

FIG. 9 and TABLE IV illustrate the effect of the gelonin immunotoxin of the present invention on H9 cells plus HIV-MN. At a dose of 1 nanogram/ml, the gelonin immunotoxin produced approximately 80% cell kill after 3 days. A 10 mg/ml dose of the gelonin immunotoxin resulted in approximately 93% cell death.

TABLE IV

| | GELONIN IMMUNOTOXIN | | | | |
|---|---|---|---|---|---|
| Days Post-Treatment | Target Cell | Media | % Dead Cells | | |
| | | | 1 | 3.4 | 10 |
| 1 | H9 | 6 | 5 | 4 | 8 |
| | H9+HIVIIIB | 7 | 30 | 29 | 46 |
| | H9+HIV MN | 5 | 15 | 16 | 21 |
| 2 | H9 | 6 | 11 | 8 | 10 |
| | H9+HIVIIIB | 6 | 40 | 44 | 61 |
| | H9+HIV MN | 5 | 31 | 30 | 37 |
| 3 | H9 | 6 | 10 | 11 | 8 |
| | H9+HIVIIIB | 7 | 80 | 91 | 90 |
| | H9+HIV MN | 7 | 79 | 78 | 95 |

H9 is the uninfected cell line. The doses of the immunotoxin are given in μg/ml.

In summary, these cytotoxicity experiments directly showed that two different monoclonal antibodies against HIV reverse transcriptase could be combined with two different types of plant toxins and lead to selective killing of cells infected with several different strains of HIV. These results illustrate that it is possible to utilize a wide variety of monoclonal antibodies against HIV reverse transcriptase and a variety of toxins, combined in immunoconjugates, to selectively inactivate HIV infected cells.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A composition of matter, comprising an immunotoxin, said immunotoxin comprising a toxin chemically conjugated to a monoclonal antibody directed against an HIV viral reverse transcriptase.

2. The composition of claim 1, wherein said toxin is selected from the group consisting of pokeweed antiviral protein, gelonin, ricin, abrin, modeccin, dodecandrin, saporin, volkensin and vicumin.

3. The composition of claim 1, wherein said immunotoxin is chemically cross-linked using a cross-linking agent selected from the group consisting of m-maleimidobenzoyl-N-hydroxysuccinimide ester (MBS), N-succinimidyl-3-(2-pyridyldithio-)-propionate (SPDP), alpha-iminothiolane hydrochloride, methyl 3-mercaptopropionimidate, Succinimidyl 4-(N maleimidomethyl) cyclohexane-1-carboxylate (SMCC), 4-succinimidyloxycarbonyl-alpha-methyl-alpha-(2-pyridydithio)-toluene (SMPT), N-succinimidyl (4-iodoacetyl)aminobenzoate (SIAB) and sulfosuccinimidyl 4-(p-maleimidophenyl)butyrate (SMPB).

* * * * *

UNITED STATES PATENT AND TRADEMARK OFFICE
CERTIFICATE OF CORRECTION

PATENT NO. : 5,645,836

DATED : Jul. 8, 1997

INVENTOR(S) : George Barrie Kitto

Page 1 of 2

It is certified that error appears in the above-identified patent and that said Letters Patent is hereby corrected as shown below:

In the Abstract, third line, "vital" should read -- viral --.

In the Abstract, fifth line, after the word "novel" the word -- immunotoxin -- should be inserted.

In the drawings, Figure 1, sixth line, "MONODONAL Ab" should read -- MONOCLONAL Ab"

Figure 2:
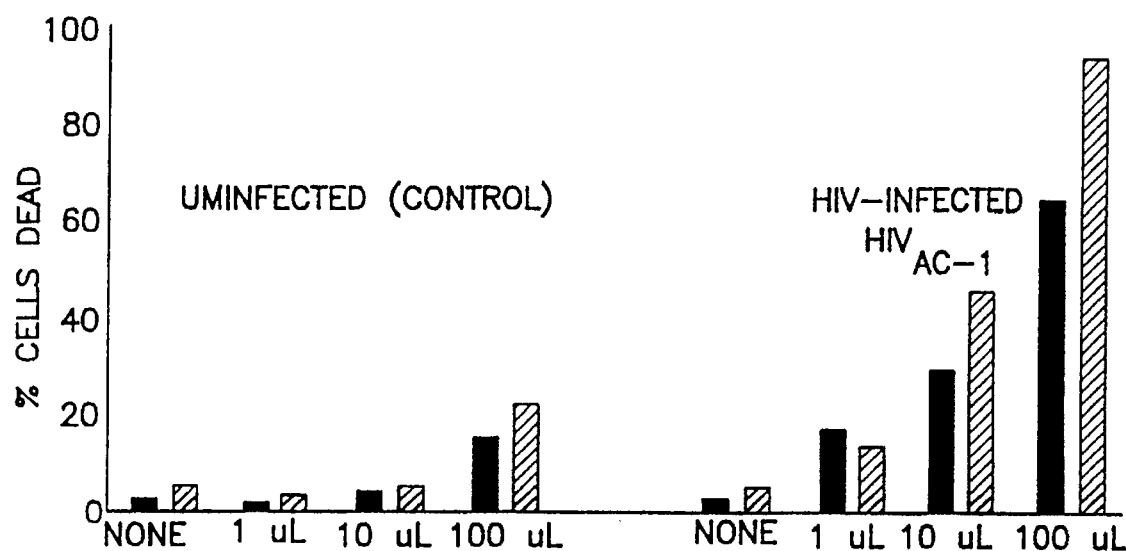

In the drawings, Figure 2, "UMINFECTED (CONTROL)" should read -- UNINFECTED (CONTROL)"

Column 3, line 27, "protein, gelonin ricin A," should read -- protein, gelonin, ricin A --.

Column 4, line 60, "is in a range" should read -- are in a range --.

Column 6, line 14, "balb/c" should read -- Balb/c --.

Column 7, line 48, "fluid from the each" should read -- fluid from each --.

Column 9, line 42, "hours incubation" should read -- hours of incubation --.

Figure 3:
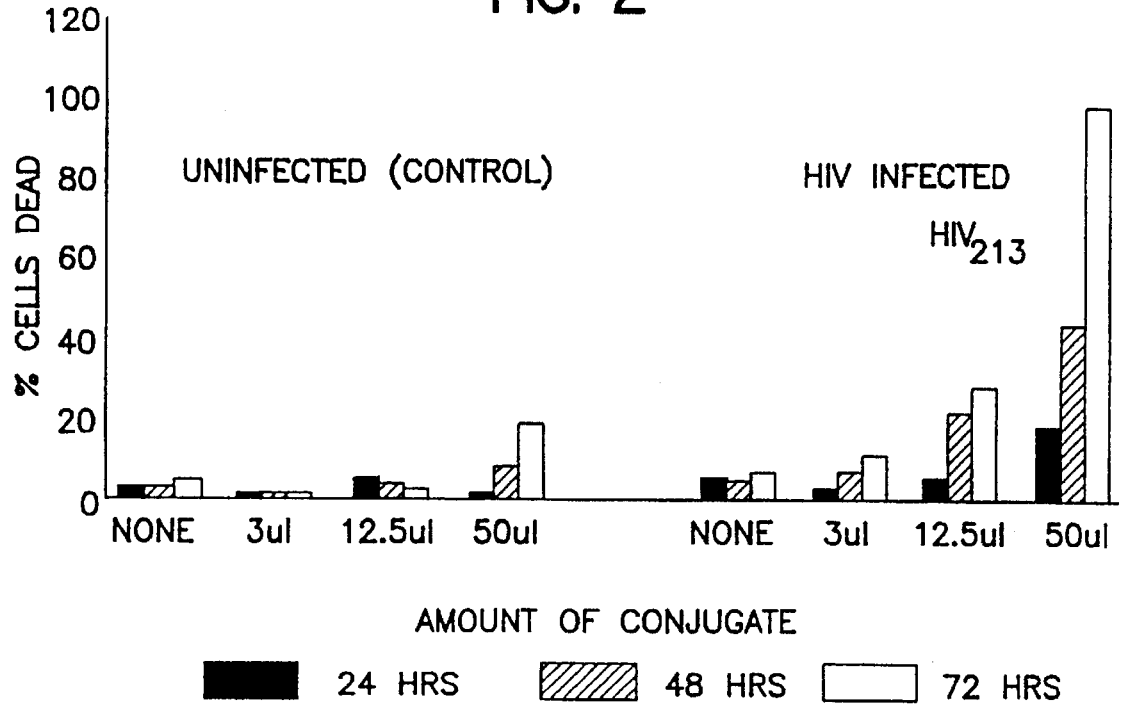
Figure 4:
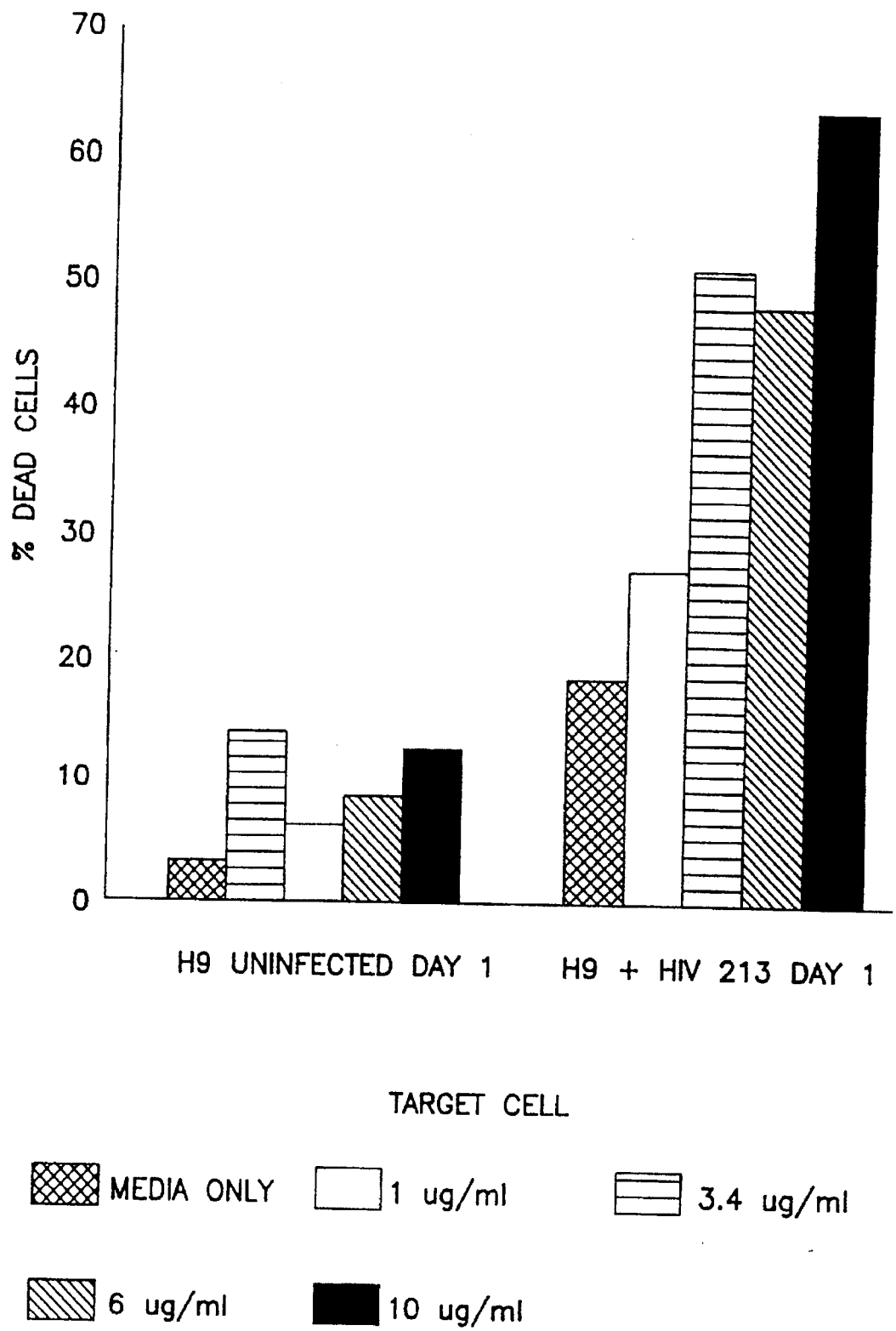
Figure 5:
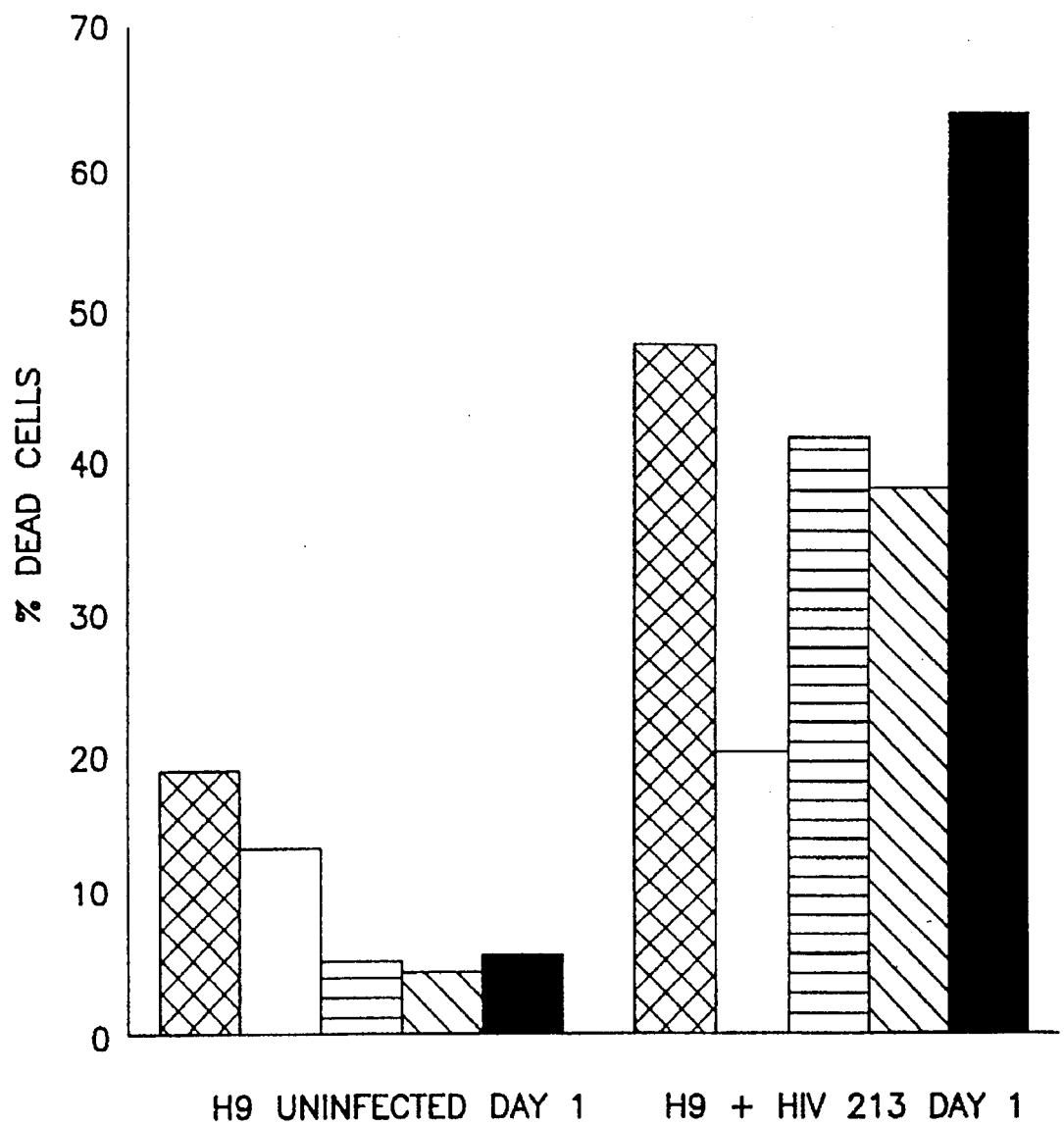
Figure 6:
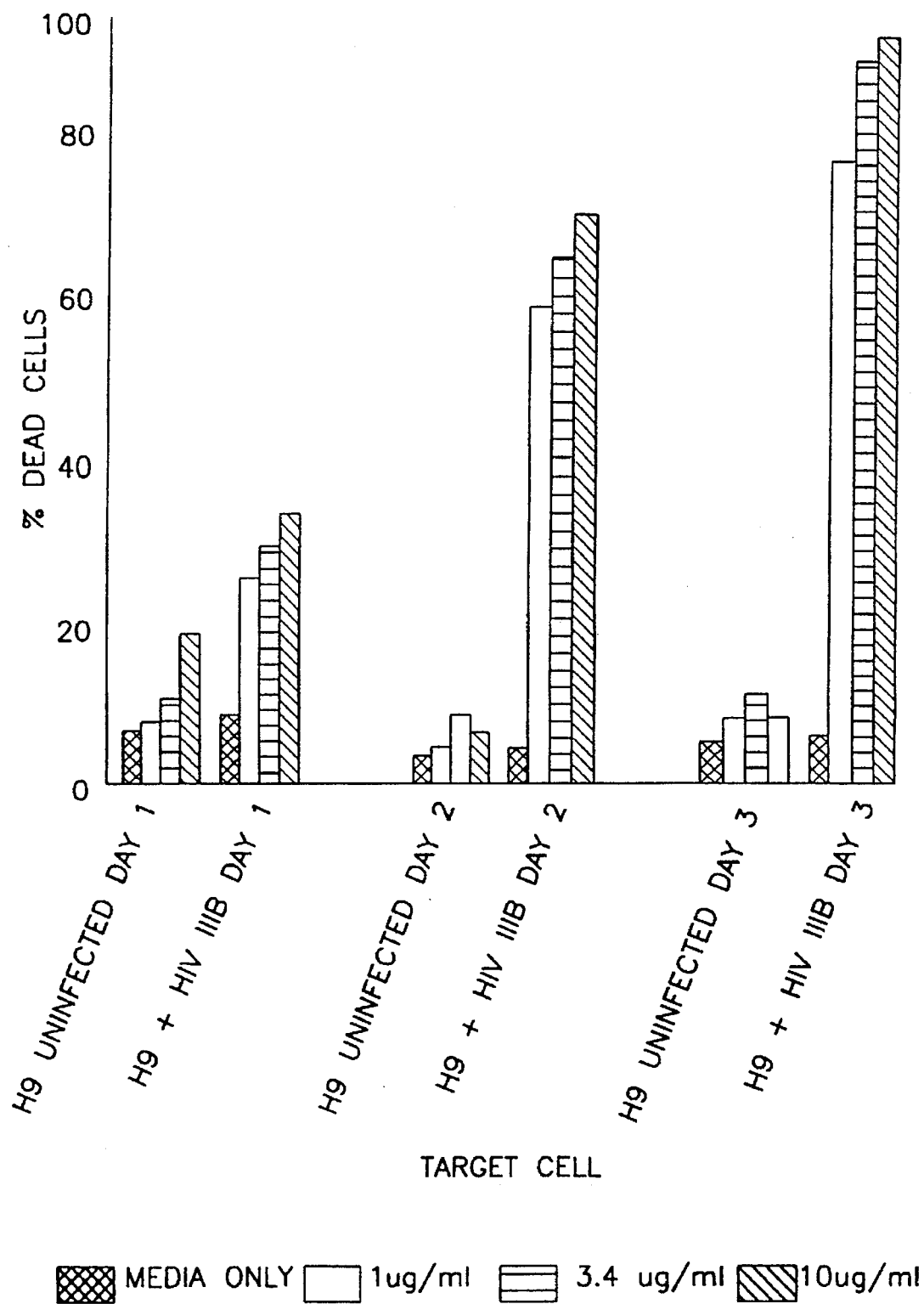

Column 9, line 59, "FIG. 3 and TABLE II shows" should read -- FIG. 3 and TABLE II show --.

UNITED STATES PATENT AND TRADEMARK OFFICE
CERTIFICATE OF CORRECTION

PATENT NO. : 5,645,836
DATED : Jul. 8, 1997
INVENTOR(S) : George Barrie Kitto

It is certified that error appears in the above-identified patent and that said Letters Patent is hereby corrected as shown below:

Column 10, line 32, "University of Texas as" should read -- University of Texas at --.

Signed and Sealed this

Twenty-first Day of April, 1998

Attest:

BRUCE LEHMAN

Attesting Officer

Commissioner of Patents and Trademarks